United States Patent
Hackett

(10) Patent No.: US 8,975,283 B2
(45) Date of Patent: Mar. 10, 2015

(54) PHARMACOLOGICALLY ACTIVE COMPOUNDS CONTAINING SULFUR

(71) Applicant: JON Pty Limited, Middle Dural (AU)

(72) Inventor: John Allen Hackett, Middle Dural (AU)

(73) Assignee: JON Pty Limited, Middle Dural (AU)

( * ) Notice: Subject to any disclaimer, the term of this patent is extended or adjusted under 35 U.S.C. 154(b) by 97 days.

(21) Appl. No.: 13/734,270

(22) Filed: Jan. 4, 2013

(65) Prior Publication Data

US 2013/0123504 A1    May 16, 2013

Related U.S. Application Data

(62) Division of application No. 12/093,917, filed as application No. PCT/AU2006/001727 on Nov. 17, 2006, now Pat. No. 8,362,041.

(30) Foreign Application Priority Data

Nov. 17, 2005    (AU) .............................. 2005906409

(51) Int. Cl.
    *A01N 43/52*    (2006.01)
    *C07D 401/04*    (2006.01)

(52) U.S. Cl.
    CPC .................... *C07D 401/04* (2013.01)
    USPC ....................................................... 514/338

(58) Field of Classification Search
    CPC .................................................. C07D 401/04
    See application file for complete search history.

(56) References Cited

U.S. PATENT DOCUMENTS

| | | | |
|---|---|---|---|
| 4,689,331 A | 8/1987 | Ankner et al. | |
| 4,766,133 A * | 8/1988 | Fischli et al. ................. | 514/338 |
| 2002/0142050 A1 | 10/2002 | Straub et al. | |
| 2008/0214618 A1 | 9/2008 | Roberton et al. | |

FOREIGN PATENT DOCUMENTS

| | | |
|---|---|---|
| DE | 199 18 434 A1 | 10/2000 |
| JP | 11-246556 | 9/1999 |
| WO | 92/09595 A1 | 6/1992 |
| WO | 2005/074536 A2 | 8/2005 |

OTHER PUBLICATIONS

Bannister, B., "(7S)-7-Deoxy-7-Substituted-Alkylthio-Lincomycins. S-Alkylation of Sulphides by an Activated Epimine Under Acidic Catalysis: Formation of α-Acetamido-Sulphides," Tetrahedron, 1984, pp. 1633-1660, vol. 40, No. 10.
Besancon, M., et al., "Sites of Reaction of the Gastric H,K-ATPase with Extracytoplasmic Thiol Reagents," The Journal of Biological Chemistry, Sep. 5, 1997, pp. 22438-22446, vol. 272, No. 36.
Brandstrom, A., et al., "Chemical Reactions of Omeprazole and Omeprazole Analogues. I. A Survey of the Chemical Transformations of Omeprazole and its Analogues," Acta Chemica Scandinavica, 1989, pp. 536-548, vol. 43.
Brandstrom, A., et al., "Chemical Reactions of Omeprazole and Omeprazole Analogues. II. Kinetics of the Reaction of Omeprazole in the Presence of 2-Mercaptoethanol," Acta Chemica Scandinavica, 1989, pp. 549-568, vol. 43.
Brandstrom, A., et al., "Chemical Reactions of Omeprazole and Omeprazole Analogues. III. Protolytic Behaviour of Compounds in the Omeprazole System," Acta Chemica Scandinavica, 1989, pp. 569-576, vol. 43.
Brandstrom, A., et al., "Chemical Reactions of Omeprazole and Omeprazole Analogues. IV. Reactions of Compounds of the Omeprazole System with 2-Mercaptoethanol," Acta Chemica Scandinavica, 1989, pp. 577-586, vol. 43 (Including Erratum).
Brandstrom, A., et al., "Chemical Reactions of Omeprazole and Omeprazole Analogues. V. The Reaction of N-Alkylated Derivatives of Omeprazole Analogues with 2-Mercaptoethanol," Acta Chemica Scandinavica, 1989, pp. 587-594, vol. 43.
Brandstrom, A., et al., "Chemical Reactions of Omeprazole and Omeprazole Analogues. VI. The Reactions of Omeprazole in the Absence of 2-Mercaptoethanol," Acta Chemica Scandinavica, 1989, pp. 565-611, vol. 43.
MedlinePlus definition of Metabolite, downloaded on Nov. 8, 2011 from <http://www.nlm.nih.gov/medlineplus/ency/article/002258.htm>, 1 page.
Minato, H., et al., "Tosylsulfonium Ions and Acylsulfonium Ions," Chemistry Letters, 1976, pp. 593-596, vol. 6.
Nenajdenko, V. G., et al., "Oxidative Properties of Triflic Anhydride. Oxidation of Alcohols and Sulfides," Journal of Organic Chemistry, 1997, pp. 2483-2486, vol. 62, No. 8.
Online Medical Dictionary definition of Derivative, downloaded on Nov. 8, 2011 from <http://medical-dictionary.thefreedictionary.com/derivative>, 2 pages.

(Continued)

*Primary Examiner* — Christina Bradley
(74) *Attorney, Agent, or Firm* — Senniger Powers LLP

(57) ABSTRACT

Disclosed herein is a method for the production of disulfide compounds of the formula I $$\text{PAC-S}^A\text{—S}^B\text{—R}^* \qquad (I)$$

wherein PAC-$S^A$ is a residue of a pharmaceutically active drug a metabolite thereof or a pharmaceutically acceptable salt thereof that is covalently bonded via the sulfur atom, $S^A$ of a reduced sulfhydryl, sulfinyl, sulfonyl or sulfonamide group to the sulfur atom $S^B$ of an oxidized sulfhydryl group of a pharmacologically acceptable sulfhydryl compound in the absence of an acid. Preferably the pharmaceutically active drug is a proton pump inhibitor and the sulfhydryl compound is N-acetyl cysteine. The disulfide compounds according to the invention can be prepared either in vitro or in vivo and are stable in the acidic conditions of the stomach. Pharmaceutical compositions containing compounds of the formula I and a method for the treatment or prophylaxis of gastrointestinal disorders using compounds of the formula I are also described.

3 Claims, 2 Drawing Sheets

(56) References Cited

OTHER PUBLICATIONS

Sturm, E., et al., "(H+-K+)-ATPase Inhibiting 2-[(2-Pyridylmethyl)sulfinyl]benzimidazoles. 1.1 Their Reaction with Thiols Under Acidic Conditions. Disulfide Containing 2-Pyridiniobenzimidazolides as Mimics for the Inhibited Enzyme," Journal of Organic Chemistry, 1987, pp. 4573-4581, vol. 52, No. 20.

Testa, B., "Prodrug Research: Futile or Fertile?," Biochemical Pharmacology, 2004, pp. 2097-2106, vol. 68.

Tutunji, M. F., et al., "An in Vitro Investigation on Acid Catalyzed Reactions of Proton Pump Inhibitors in the Absence of an Electrophile," International Journal of Pharmaceuticals, 2006, pp. 110-116, vol. 323.

Weidolf, L., et al., "A Metabolic Route of Omeprazole Involving Conjugation with Glutathione Identified in the Rat," Drug Metabolism and Disposition, 1992, pp. 262-267, vol. 20, No. 2.

* cited by examiner

PHARMACOLOGICALLY ACTIVE COMPOUNDS CONTAINING SULFUR

CROSS-REFERENCE TO RELATED APPLICATIONS

This application is a divisional of U.S. patent application Ser. No. 12/093,917, filed Sep. 5, 2008, which is a U.S. PCT National Patent Application of PCT/AU2006/001727, filed Nov. 17, 2006, which claims the priority of Australian Patent Application No. 2005906409, filed Nov. 17, 2005, the entirety of which are herein incorporated by reference.

FIELD OF INVENTION

This invention relates to pharmacologically active compounds containing sulfur which can be transformed to pharmacologically active di-sulfide compounds, and to methods for preparing the same in vitro or formulating to allow for in vivo formation of the di-sulfide compounds. The compounds according to this invention are preferably formed between a pharmaceutically active compound containing a thiol (sulfhydryl), sulfinyl, sulfonyl or sulfonamide group and a pharmacologically acceptable thiol compound.

BACKGROUND

Sulfur in organic compounds plays a varied and critical role in biological systems. The simple sulfur containing amino acid cysteine is a significant protein building block. It participates in complex metal binding roles, binding to other sulfur groups, protein folding bonding and reduction-oxidation (REDOX) functions. Sulfur atoms are also an important part of amino acid building blocks of peptides, proteins, enzymes, membranes, nucleic acids and DNA.

Many pharmaceutically active compounds (PACs) contain a thiol (sulfhydryl), sulfinyl (SO), sulfonyl ($SO_2$) or sulfonamide (SONR'R' where R' is hydrogen or alkyl) group which undergoes oxidation-reduction (REDOX) reactions with thiol (sulfhydryl), disulfide, sulfinyl or sulfonyl groups attached to proteins, enzymes (eg gastric H, K, ATPase), peptides (e.g. glutathione) or simple molecules (eg cysteine). The binding of the PAC to these groups is a reversible process influenced by a number of factors, including pH, presence of other oxidising and reducing groups, physiological REDOX buffer systems, REDOX catalysts, enzymes, and temperature.

In most physiological systems there is a need to maintain a healthy dynamic REDOX balance both inside and outside cells.

The sulfur group of PACs may be particularly important to drug activity. The range of activities of PACs containing sulfur groups cover anti-bacterial, anti-inflammatory, anti-rheumatic, anti-ulcer, anti-viral, anti-psychotic, mucolytic, hepatoprotectant, diuretic, fungicidal, diabetic activities amongst others. The extent of sulfur group content in PACs indicates the biological/pharmacological significance of sulfur content in drug molecules.

Examples of pharmaceutically active compounds (PACs) containing sulfinyl, sulfonyl or sulfonamide groups include proton pump inhibitors (PPIs) and compounds having anti-ulcerant activity, such as Omeprazole, Omeprazole isomers such as S-Omeprazole, Esomeprazole (Nexium®), R-Omeprazole, Lansoprazole, Pantoprazole, Rabeprazole, Pariprazole, Tenatoprazole, Leminoprazole and their isomers or metabolites.

However, despite their biological activity and pharmaceutical benefit, PACs containing sulfur groups are typically relatively unstable, can present formulation difficulties, and/or be of low bioavailability.

Sulfur containing PACs may also be unstable in the acid environment of the stomach. Examples include the proton pump inhibitors (PPIs) such as Omeprazole. Elaborate and costly formulations have been developed and continue to be developed in attempts to address these problems (see for example WO 94/25070, WO 00/27366 and AU 13541/00). Thus, there is a need for a PPI formulation that does not involve an enteric coat but is still stable under stomach acidic conditions.

SUMMARY OF THE INVENTION

In accordance with a first aspect of this invention there is provided a method for the production of a compound of the formula I

$$PAC\text{-}S^A\text{---}S^B\text{---}R^* \quad (I)$$

wherein

PAC-$S^A$ is a residue of a pharmaceutically active drug metabolite thereof or a pharmaceutically acceptable salt thereof containing a covalently bonded sulfur atom $S^A$ in the form of a reduced sulfhydryl, sulfinyl, sulfonyl or sulfonamide group wherein $S^A$ is covalently bonded to a sulfur atom $S^B$ of an oxidised sulfhydryl group of a pharmacologically acceptable sulfhydryl compound and R* represents alkyl, cycloalkyl, aryl, arylalkyl, alkylthio, alkoxy, alkoxyalkoxy, dialkylamino, piperidino, morpholine, phenylalkyl, phenylalkoxy, carboxylic acid or amino that is optionally substituted by one or more substituents selected from alkyl, cycloalkyl, aryl, arylalkyl, alkylthio, alkoxy, alkoxyalkoxy, dialkylamino, piperidino, morpholine, phenylalkyl, phenylalkoxy, carboxylic acid, acetamide, hydroxyl, halogen, —CN, —$CF_3$, —$NO_2$ or R* represents an amino acid, acetylated amino acid, peptide, protein or a derivative thereof, the method comprising reacting a PAC containing a sulfhydryl, sulfinyl, sulfonyl or sulfonamide group, with a pharmacologically acceptable sulfhydryl compound in the absence of acid at a molar ratio of PAC to sulfhydryl compound of at least 1:2 to 1:10 to form a compound of the formula I.

In accordance with a second aspect of the invention there is provided a compound prepared by the method according to the first aspect of the invention.

In accordance with a third aspect of the invention there is provided a compound having the structure (A):

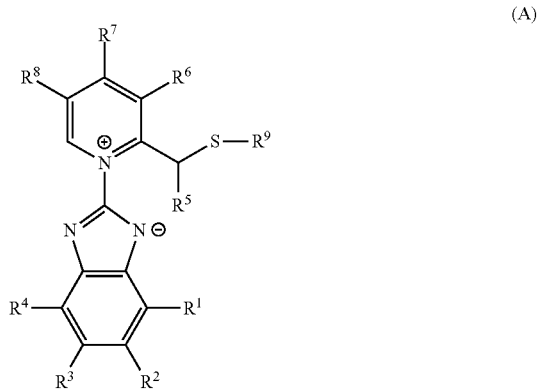

wherein $R^1$, $R^2$, $R^3$ and $R^4$ are the same or different and are hydrogen, an alkyl, cycloalkyl, alkoxy, alkoxyalkyl, alkoxyalkoxy, halogen, —CN, —$CF_3$, —$NO_2$, —$COR^{10}$, alkylthio, alkylsulfinyl, aryl, arylalkyl, aryloxy or arylalkoxy group, or wherein $R^1$ and $R^2$, $R^2$ and $R^3$, or $R^3$ and $R^4$ together with the adjacent carbon atoms in the benzimidazole ring form one or more 5-, 6- or 7-membered rings, which each may be saturated or unsaturated and may contain 0-3 hetero atoms selected from N, S and O, and each ring may be optionally substituted with 1-4 substituents selected from alkyl groups with 1-3 carbon atoms, or two or four of the mentioned substituents together form one or two oxo groups

or $R^1$ and $R^2$, $R^2$ and $R^3$ or $R^3$ and $R^4$ together with the adjacent carbon atoms in the benzimidazole ring form two rings condensed with each other;

$R^5$, $R^6$ and $R^8$ are the same or different and are selected from hydrogen and alkyl;

$R^7$ is hydrogen, an alkyl, alkoxy, aryl, arylalkyl, aryloxy, arylalkoxy, alkenyloxy or alkynyloxy group; or $R^6$ and $R^7$, or $R^7$ and $R^8$ together with the adjacent carbon atoms in the pyridine ring form a 5- or 6-membered, saturated or unsaturated ring, which may optionally contain an oxygen or an optionally alkylated nitrogen atom, $R^{10}$ represents alkyl, aryl, aryloxy and alkoxy, and $R^9$ is a radical of a pharmacologically acceptable sulfhydryl compound, wherein the sulfhydryl compound is selected from the group consisting of N-acetyl-cysteine, penicillamine, thioalkl(alkene)ols, thiosorbitol, thioglycerol, thioglucose, thioacetic acid, thiomalic acid, thiopolyoxyethanols, thiopolyalkoxyethanols, thiouracil, thioguanosine, thiolhistidine and thionalide.

In accordance with a fourth aspect of the invention there is provided a compound having the structure (V):

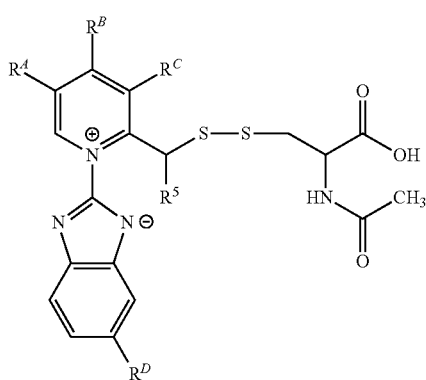

wherein:
$R^A$, $R^B$ and $R^C$ independently represent hydrogen, $C_{1-6}$ alkyl, $C_{1-6}$ alkoxy, $C_{3-6}$ cycloalkyl, $C_{3-6}$ cycloalkoxy, $C_{1-6}$ fluoroalkyl or $C_{1-6}$ fluoroalkoxy; and $R^D$ represents hydrogen, $C_{1-6}$ alkyl, $C_{1-6}$ alkoxy, $C_{1-6}$ fluoroalkyl or $C_{1-6}$ fluoroalkoxy or halogen, and $R^5$ represents hydrogen or alkyl.

In accordance with a fifth aspect of the invention there is provided a method for the in vitro production of a compound of the formula I $PAC-S^A—S^B—R*$ (I)

wherein $PAC-S^A$ is a residue of a pharmaceutically active drug metabolite thereof or a pharmaceutically acceptable salt thereof containing a covalently bonded sulfur atom $S^A$ in the form of a reduced sulfhydryl, sulfinyl, sulfonyl or sulfonamide group wherein $S^A$ is covalently bonded to a sulfur atom $S^B$ of an oxidised sulfhydryl group of a pharmacologically acceptable sulfhydryl compound and $R*$ represents alkyl, cycloalkyl, aryl, arylalkyl, alkylthio, alkoxy, alkoxyalkoxy, dialkylamino, piperidino, morpholine, phenylalkyl, phenylalkoxy, carboxylic acid or amino that is optionally substituted by one or more substituents selected from alkyl, cycloalkyl, aryl, arylalkyl, alkylthio, alkoxy, alkoxyalkoxy, dialkylamino, piperidino, morpholine, phenylalkyl, phenylalkoxy, carboxylic acid, acetamide, hydroxyl, halogen, —CN, —$CF_3$, —$NO_2$ or $R*$ represents an amino acid, acetylated amino acid, peptide, protein or a derivative thereof, the method comprising reacting a PAC containing a sulfhydryl, sulfinyl, sulfonyl or sulfonamide group, with a pharmacologically acceptable sulfhydryl compound in the absence of acid at a molar ratio of PAC to sulfhydryl compound of at least 1:2 to 1:10 to form compounds of the formula I in vitro.

In accordance with a sixth aspect of the invention there is provided a compound prepared by the method according to the fifth aspect of the invention.

According to a seventh aspect of the invention there is provided a method for the in vivo production of a compound of the formula I $PAC-S^A—S^B—R*$ (I)

wherein $PAC-S^A$ is a residue of a pharmaceutically active drug a metabolite thereof or a pharmaceutically acceptable salt thereof containing a covalently bonded sulfur atom $S^A$ in the form of a reduced sulfhydryl, sulfinyl, sulfonyl or sulfonamide group wherein $S^A$ is covalently bonded to a sulfur atom $S^B$ of an oxidised sulfhydryl group of a pharmacologically acceptable sulfhydryl compound, and $R*$ represents alkyl, cycloalkyl, aryl, arylalkyl, alkylthio, alkoxy, alkoxyalkoxy, dialkylamino, piperidino, morpholine, phenylalkyl, phenylalkoxy, carboxylic acid or amino that is optionally substituted by one or more substituents selected from alkyl, cycloalkyl, aryl, arylalkyl, alkylthio, alkoxy, alkoxyalkoxy, dialkylamino, piperidino, morpholine, phenylalkyl, phenylalkoxy, carboxylic acid, acetamide, hydroxyl, halogen, —CN, —$CF_3$, —$NO_2$ or $R*$ represents an amino acid, acetylated amino acid, peptide, protein or a derivative thereof, the method comprising mixing a PAC containing a sulfhydryl, sulfinyl, sulfonyl or sulfonamide group, with a pharmacologically acceptable sulfhydryl compound at a molar ratio of PAC to sulfhydryl compound of at least 1:2 to 1:10 and optionally one or more auxiliaries or excipients in the absence of acid which after administration to a subject allows for in vivo formation of compounds of the formula I. In one embodiment the PAC is in a dry powder form that is blended with a sulfhydryl compound that is also in dry powder form together with optionally one or more auxiliaries or excipients.

In accordance with an eighth aspect of the invention, there is provided a compound prepared by the method according to the seventh aspect of the invention.

In accordance with an ninth aspect of the invention, there is provided a composition comprising one or more compounds according to any one of the second, third, fourth, sixth or eighth aspects of the invention together with one or more auxiliaries or excipients.

In accordance with a tenth aspect of the invention, there is a formulation for the in vivo production of one or more compounds according to any one of the second, third, fourth, sixth or eighth aspects of the invention. The formulation may be in the form of a dry powder, tablet, liquid, emulsion, suppository, solution, plaster, gel, paste, granule, pellet, capsule, injectable, as well as confectionary and foodstuffs. In particular embodiments, the dry formulation or tablet formulation may include either Omeprazole, Pantoprazole, Lansoprazole, Rabeprazole or a pharmaceutically acceptable salt thereof as the PAC and N-acetyl cysteine as the sulfhydryl compound.

In accordance with an eleventh aspect of the invention, there is provided an injectable formulation for the in vitro production of one or more compounds according to any one of the second, third, fourth, sixth or eighth aspects of the invention. The injectable formulation may include either Omeprazole, Pantoprazole, Lansoprazole, Rabeprazole or a pharmaceutically acceptable salt thereof as the PAC and N-acetyl cysteine as the sulfhydryl compound.

In accordance with a twelfth aspect of the invention, there is provided a method for the treatment or prophylaxis of gastrointestinal disorders by administering to one or more compounds according to any one of the second, third, fourth, sixth or eighth aspects of the invention.

The compounds according to the invention have useful pharmacological properties such as pronounced inhibitory effect on the secretion of gastric acid and gastrointestinal protective action in animals, including humans. Due to their unique stability characteristics, the formulations and compounds according to the invention are particularly suited for the production of stable PPI dosage forms without the need for an enteric coating. They are highly suitable for use in human and veterinary medicine, where they may be used, in particular, for the treatment and/or prophylaxis of gastrointestinal disorders.

DETAILED DESCRIPTION

Figure 1:
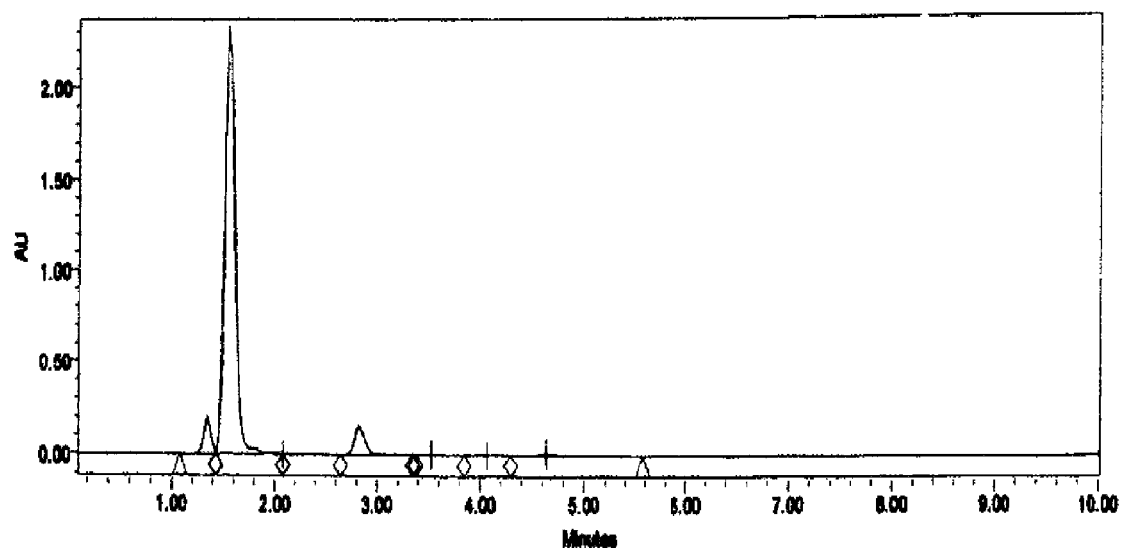
FIG. 1 shows the high performance liquid chromatograph for a sample of an Omeprazole-N-acetyl cysteine disulfide solution that was prepared in vitro in accordance with Example 3.

The present invention relates to methods of preparing disulfide compounds formed between PACs containing a sulfhydryl, sulfinyl, sulfonyl or sulfonamide group and a sulfhydryl group of a pharmacologically acceptable sulfhydryl compound in the absence of acid under in vitro or in vivo conditions. This has the effect of stabilising the normally acid labile PPI in an acidic stomach environment without the need for an enteric or oil coated type formulation. This is particularly beneficial with regard to the formulation cost, stability, bioavailability, and toxicity of the PACs. Further the use of thiol reactive molecules such as N-acetyl cysteine as the pharmacologically acceptable sulfhydryl compound enhancing the pharma-kinetics of the desired pharmaceutical effect because such compounds exhibit rapid di-sulfide REDOX exchange.

The invention provides a method for the production of one or more compounds of the formula I $$PAC\text{-}S^A\text{---}S^B\text{---}R^* \quad \quad (I)$$

wherein

PAC-$S^A$ is a residue of a pharmaceutically active drug metabolite thereof or a pharmaceutically acceptable salt thereof containing a covalently bonded sulfur atom $S^A$ in the form of a reduced sulfhydryl, sulfinyl, sulfonyl or sulfonamide group wherein $S^A$ is covalently bonded to a sulfur atom $S^B$ of an oxidised sulfhydryl group of a pharmacologically acceptable sulfhydryl compound and $R^*$ represents alkyl, cycloalkyl, aryl, arylalkyl, alkylthio, alkoxy, alkoxyalkoxy, dialkylamino, piperidino, morpholine, phenylalkyl, phenylalkoxy, carboxylic acid or amino that is optionally substituted by one or more substituents selected from alkyl, cycloalkyl, aryl, arylalkyl, alkylthio, alkoxy, alkoxyalkoxy, dialkylamino, piperidino, morpholine, phenylalkyl, phenylalkoxy, carboxylic acid, acetamide, hydroxyl, halogen, —CN, —$CF_3$, —$NO_2$ or $R^*$ represents an amino acid, acetylated amino acid, peptide, protein or a derivative thereof, the method comprising reacting a PAC containing a sulfhydryl, sulfinyl, sulfonyl or sulfonamide group, with a pharmacologically acceptable sulfhydryl compound in the absence of acid at a molar ratio of PAC to sulfhydryl compound of at least 1:2 to 1:10 to form a compound of the formula I.

In accordance with the present invention, any pharmaceutically active compound, which contains a sulfhydryl, sulfinyl, sulfonyl or sulfonamide group may be utilised as the group PAC-$S^A$ in formula I where $S^A$ represents the reduced sulfur atom of the sulfhydryl, sulfinyl, sulfonyl or sulfonamide group. Compounds of Formula I could therefore include an anti-inflammatory, antirheumatic or anti viral compounds as the PAC. For the purposes of this invention, pharmaceutically acceptable salts of PACs are also included. For example, the sodium, potassium, calcium, magnesium and zinc salts of proton pump inhibitors are also included within the definition of a PAC. The PAC may be bonded to the $S^A$ atom through one or more covalent bonds.

Examples of PACs which may be utilised in the present invention include anti-ulcerant agents such as Omeprazole, Omeprazole isomers such as S-Omeprazole, Esomeprazole (Nexium®), R-Omeprazole, Lansoprazole, Pantoprazole, Rabeprazole, Pariprazole, Leminoprazole, Tenatoprazole and their isomers, pharmaceutically acceptable salts or metabolites.

$S^B$ is a sulfur atom of an oxidised sulfhydryl group of a pharmacologically acceptable sulfhydryl compound. $S^B R^*$ in formula I represents a radical of pharmacologically acceptable sulfhydryl compound, for example of the formula:

$$HS^B R^*$$

wherein

R* represents alkyl, cycloalkyl, aryl, arylalkyl, alkylthio, alkoxy, alkoxyalkoxy, dialkylamino, piperidino, morpholine, phenylalkyl, phenylalkoxy, carboxylic acid or amino that is optionally substituted by one or more substituents selected from alkyl, cycloalkyl, aryl, arylalkyl, alkylthio, alkoxy, alkoxyalkoxy, dialkylamino, piperidino, morpholine, phenylalkyl, phenylalkoxy, carboxylic acid, acetamide, hydroxyl, halogen, CN, —CF$_3$, —NO$_2$ or R* represents an amino acid, acetylated amino acid, peptide, protein or a derivative thereof.

Non-limiting examples of pharmacologically acceptable sulfhydryl compounds which may be utilised according to this invention include L-cysteine, N-acetyl-cysteine, cysteamine, penicillamine, glutathione thioethanol, thioalkl(alkene)ols, thiosorbitol, thioglycerol, thioglucose, thioglycollic acid, thioacetic acid, thiolactic acid, thiomalic acid, thiopolyoxyethanols, thiopolyalkoxyethanols, thiouracil, thioguanosine, thiolhistidine, thionalide, and thiosalicyclic acid.

The sulfhydryl group of such compounds forms a disulfide bond with the sulfhydryl, sulfinyl, sulfonyl or sulfonamide group of the PAC. Many sulfhydryl compounds have a well established record of pharmacological interaction in their own right with clinically significant benefits including N-Acetyl Cysteine and glutathione.

In particular embodiments R* represents:

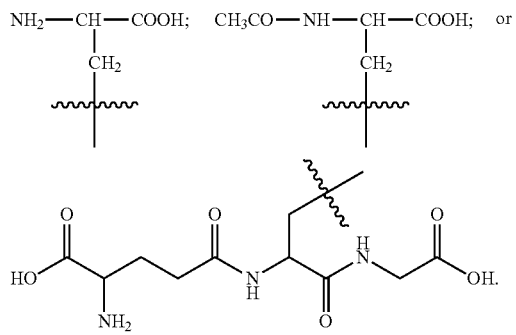

In particular embodiments R*S$^B$H is cysteine, N-acetyl cysteine or glutathione.

The invention also provides for a number of compounds such as formula IA

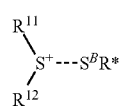

(IA)

-ve counter ion wherein:
R$^{11}$, R$^{12}$ and S$_+$ together represent a residue of a pharmaceutically active compound; and
S$^B$R* represents a radical of a pharmacologically acceptable sulfhydryl compound. Non-limiting examples of S$^B$R* include L-cysteine, N-acetyl-cysteine, cysteamine, penicillamine, glutathione, thioethanol, thioalkl(alkene)ols, thiosorbitol, thioglycerol, thioglucose, thioglycollic acid, thioacetic acid, thiolactic acid, thiomalic acid, thiopolyoxyethanols, thiopolyalkoxyethanols, thiouracil, thioguanosine, thiolhistidine, thionalide and thiosalicyclic acid.

Where the sulfur atom has a positive charge to balance the overall charge of the molecule a -ve counter ion will be present. Negative ions include those known to persons skilled in the art and may be derived from one or more of the following; halogen such as chloro, bromo or iodo, acetic acid, ascorbic acid, aspartic acid, benzoic acid, benzenesulfonic acid, citric acid, cinnamic acid, ethanesulfonic acid, fumaric acid, glutamic acid, glutaric acid, gluconic acid, hydrochloric acid, hydrobromic acid, lactic acid, maleic acid, malic acid, methanesulfonic acid, naphthoic acid, hydroxynaphthoic acid, naphthalenesulfonic acid, naphthalenedisulfonic acid, naphthaleneacrylic acid, oleic acid, oxalic acid, oxaloacetic acid, phosphoric acid, pyruvic acid, p-toluenesulfonic acid, tartaric acid, trifluoroacetic acid, triphenylacetic acid, tricarballylic acid, salicylic acid, sulfuric acid, sulfamic acid, sulfanilic acid and succinic acid.

In one embodiment the counter ion is chloride.

The present invention also relates to a compound of the formula I having the structure (A):

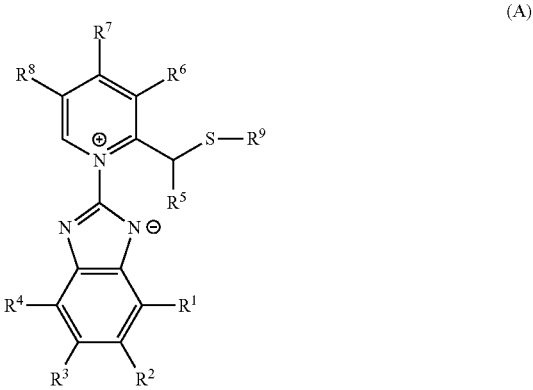

(A)

wherein R$^1$, R$^2$, R$^3$ and R$^4$ are the same or different and are hydrogen, an alkyl, cycloalkyl, alkoxy, alkoxyalkyl, alkoxyalkoxy, halogen, —CN, —CF$_3$, —NO$_2$, —COR$^{10}$, alkylthio, alkylsulfinyl, aryl, arylalkyl, aryloxy or arylalkoxy group, or wherein R$^1$ and R$^2$, R$^2$ and R$^3$, or R$^3$ and R$^4$ together with the adjacent carbon atoms in the benzimidazole ring form one or more 5-, 6- or 7-membered rings, which each may be saturated or unsaturated and may contain 0-3 hetero atoms selected from N, S and O, and each ring may be optionally substituted with 1-4 substituents selected from alkyl groups with 1-3 carbon atoms, or two or four of the mentioned substituents together form one or two oxo groups

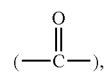

or R$^1$ and R$^2$, R$^2$ and R$^3$ or R$^3$ and R$^4$ together with the adjacent carbon atoms in the benzimidazole ring form two rings condensed with each other;
R$^5$, R$^6$ and R$^8$ are the same or different and are selected from hydrogen and alkyl;
R$^7$ is hydrogen, an alkyl, alkoxy, aryl, arylalkyl, aryloxy, arylalkoxy, alkenyloxy or alkynyloxy group; or
R$^6$ and R$^7$, or R$^7$ and R$^8$ together with the adjacent carbon atoms in the pyridine ring form a 5- or 6-membered, saturated or unsaturated ring, which may optionally contain an oxygen or an optionally alkylated nitrogen atom,
R$^{10}$ represents alkyl, aryl, aryloxy and alkoxy, and
R$^9$ is a radical of a pharmacologically acceptable sulfhydryl compound, wherein the sulfhydryl compound is selected from the group consisting of N-acetyl-cysteine, penicillamine, thioalkl(alkene)ols, thiosorbitol, thioglycerol, thioglucose, thioacetic acid, thiomalic acid, thiopolyoxyethanols, thiopolyalkoxyethanols, thiouracil, thioguanosine, thiolhistidine and thionalide.

The present invention also provides compounds of the formula IB

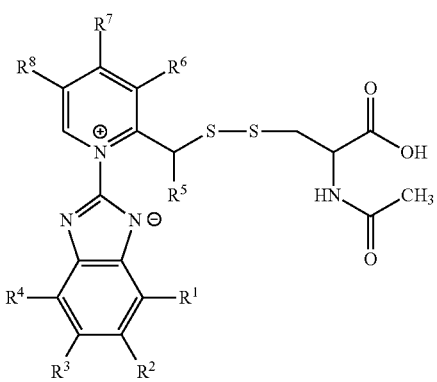

(IB)

wherein $R^1$, $R^2$, $R^3$ and $R^4$ are the same or different and are hydrogen, an alkyl, cycloalkyl, alkoxy, alkoxyalkyl, alkoxyalkoxy, halogen, —CN, —CF$_3$, —NO$_2$, —COR$^{10}$, alkylthio, alkylsulfinyl, aryl, arylalkyl, aryloxy or arylalkoxy group, or $R^1$ and $R^2$, $R^2$ and $R^3$, or $R^3$ and $R^4$ together with the adjacent carbon atoms in the benzimidazole ring form one or more 5-, 6- or 7-membered rings, which each may be saturated or unsaturated and may contain 0-3 hetero atoms selected from N, S and O, and each ring may be optionally substituted with 1-4 substituents selected from alkyl groups with 1-3 carbon atoms, or two or four of the mentioned substituents together form one or two oxo groups

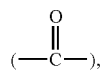

or if $R^1$ and $R^2$, $R^2$ and $R^3$ or $R^3$ and $R^4$ together with the adjacent carbon atoms in the benzimidazole ring form two rings these rings may be condensed with each other;

$R^5$, $R^6$ and $R^8$ are the same or different and are selected from hydrogen and alkyl;

$R^7$ is hydrogen, an alkyl, alkoxy, aryl, arylalkyl, aryloxy, arylalkoxy, alkenyloxy or alkynyloxy group; or $R^6$ and $R^7$, or $R^7$ and $R^8$ together with the adjacent carbon atoms in the pyridine ring form a 5- or 6-membered, saturated or unsaturated ring, which may optionally contain an oxygen or an optionally alkylated nitrogen atom, and $R^{10}$ represents alkyl, aryl, aryloxy and alkoxy.

As used herein the term "alkyl" is taken to include straight chain and branched chain saturated alkyl groups of 1 to 6 carbon atoms, such as methyl, ethyl, propyl, isopropyl, butyl, isobutyl, secbutyl, tertiary butyl, pentyl and the like. The alkyl group more preferably contains preferably from 1 to 4 carbon atoms, especially methyl, ethyl, propyl or isopropyl.

As used herein the term "alkoxy" also includes a straight chain and branched chain saturated alkyl groups of 1 to 6 carbon atoms.

Cycloalkyl includes C$_{3-6}$ cycloalkyl such as cyclopropyl, cyclobutyl, cyclopentyl and cyclohexyl.

As used herein the term "aryl" is taken to include phenyl, benzyl, biphenyl and naphthyl and may be optionally substituted by one or more C$_1$-C$_4$-alkyl, hydroxy, C$_1$-C$_4$-alkoxy, carbonyl, C$_1$-C$_4$-alkoxycarbonyl, C$_1$-C$_4$-alkylcarbonyloxy, nitro or halo.

As used herein the term "halogen" means fluorine, bromine, chlorine or iodine.

"Disulfide bond" as used in the context of this specification means any covalent bond between two sulfur atoms.

"Gastrointestinal protection" as used in the present context means the prevention and treatment of gastrointestinal disorders, in particular gastrointestinal inflammatory disorders and lesions such as, for example, Ulcus ventriculi, Ulcus duodeni, gastritis, irritable bowel owing to an increased production of acid or as a result of medicaments, GERD, Crohn's disease, IBD. Such disorders may be caused, for example, by microorganisms such as Helicobacter pylori, bacterial toxins, medicaments such as certain antiphlogistics and antirheumatic drugs, chemicals such as ethanol, gastric acid or stress.

In accordance with the present invention, compounds of the formula I are formed by a reaction between a PAC containing a sulfhydryl, sulfinyl, sulfonyl or sulfonamide group with a pharmacologically acceptable sulfhydryl compound either in vitro or in vivo. The reaction in vitro can occur in an aqueous solution, in a polar protic solvent such as methanol, ethanol, butanol or a mixture of water and polar protic solvent without the addition of an acid. In one embodiment, the reaction in vitro is carried out in an aqueous solution at a molar ratio of PAC to pharmacologically acceptable sulfhydryl compound of at least 1:2 to 1:10. Compounds of the formula I can also be prepared in vivo by mixing a PAC containing a sulfhydryl, sulfinyl, sulfonyl or sulfonamide group with a pharmacologically acceptable sulfhydryl compound at a molar ratio of PAC to pharmacologically acceptable sulfhydryl compound of at least 1:2 to 1:10 and optionally one ore more auxiliaries or excipients without the addition of an acid. In one embodiment the PAC is in a dry powder form that is blended with a sulfhydryl compound that is also in dry powder form. Administration of the mixture or dry powder blend to a subject allows for the in vivo formation of the compounds of formula I.

The resulting compounds of the formula I are water soluble, and may be concentrated by standard techniques such as chromatography (including high performance liquid chromatography (HPLC) or column chromatography), diafiltration, or evaporation. Alternatively, compounds of the formula I may be recrystallised from solution according to standard techniques.

Examples of PACs which may be used in accordance with the invention are proton pump inhibitors (PPIs) of the general formula B shown below:

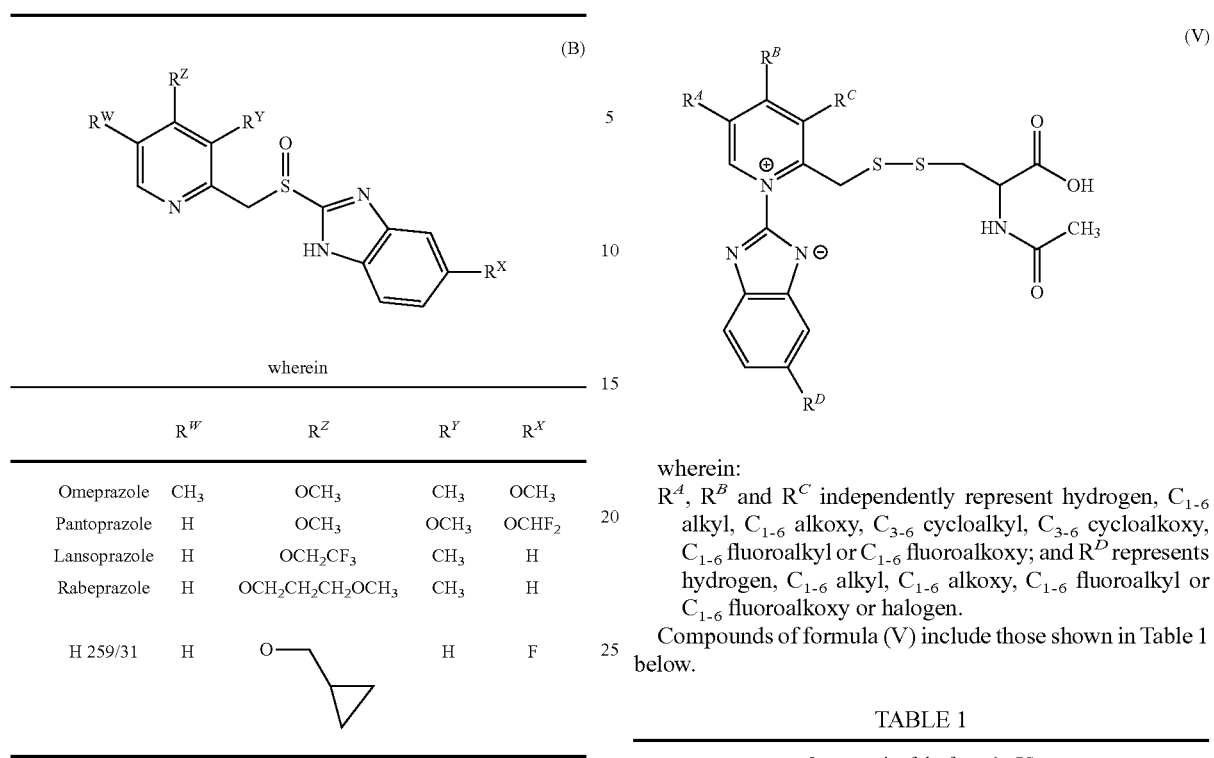

(B)

wherein

| | $R^W$ | $R^Z$ | $R^Y$ | $R^X$ |
|---|---|---|---|---|
| Omeprazole | $CH_3$ | $OCH_3$ | $CH_3$ | $OCH_3$ |
| Pantoprazole | H | $OCH_3$ | $OCH_3$ | $OCHF_2$ |
| Lansoprazole | H | $OCH_2CF_3$ | $CH_3$ | H |
| Rabeprazole | H | $OCH_2CH_2CH_2OCH_3$ | $CH_3$ | H |
| H 259/31 | H | O—⟨cyclopropyl⟩ | H | F |

As shown above, the sulfur group of the PPIs may be in the sulfinyl form and is linked through two covalent bonds to the rest of the PAC structure.

The structure and synthesis of PPIs are disclosed in the following patents, which are incorporated herewith by reference: Omeprazole is disclosed in U.S. Pat. No. 4,255,431 and EP0005129, Pantoprazole is disclosed in U.S. Pat. No. 4,758,579 and EP 166287, Lanzoprazole is disclosed in U.S. Pat. No. 4,628,098 and EP174726, Leminoprazole is disclosed in GB 2163737, Tenatoprazole is disclosed in EP254588 and Rabeprazole is disclosed in U.S. Pat. No. 5,045,552.

These PPIs are all substituted benzimidazoles and have the same mechanism of action. They are distinctive in that under acidic conditions, protonation of the pyridine and benzimidazole nitrogens results in formation of a tetracycline sulfenamide with a terminal thiol group, which is the active form of the drug binding to exposed cysteine residues on the hydrogen-potassium ATPase enzyme system at the surface of the gastric parietal cells to form covalent disulfide bonds that inhibit the activity of the pump.

The structure and synthesis of other PACs are described in the literature as indicated above, and will be known to those skilled in the art.

In particular embodiments of the invention the PACs employed are Omeprazole, Omeprazole isomers such as S-Omeprazole, Esomeprazole (Nexium®), R-Omeprazole, Lansoprazole, Pantoprazole, Rabeprazole, Pariprazole, Leminoprazole, Tenatoprazole and their isomers, pharmaceutically acceptable salts or metabolites.

In particular embodiments of the invention compounds of the formula (I) having a structure (V):

wherein:
$R^A$, $R^B$ and $R^C$ independently represent hydrogen, $C_{1-6}$ alkyl, $C_{1-6}$ alkoxy, $C_{3-6}$ cycloalkyl, $C_{3-6}$ cycloalkoxy, $C_{1-6}$ fluoroalkyl or $C_{1-6}$ fluoroalkoxy; and $R^D$ represents hydrogen, $C_{1-6}$ alkyl, $C_{1-6}$ alkoxy, $C_{1-6}$ fluoroalkyl or $C_{1-6}$ fluoroalkoxy or halogen.

Compounds of formula (V) include those shown in Table 1 below.

TABLE 1

Compounds of the formula (V)

| COMPOUND | $R^A$ | $R^B$ | $R^C$ | $R^D$ |
|---|---|---|---|---|
| $V^1$ | $CH_3$ | $OCH_3$ | $CH_3$ | $OCH_3$ |
| $V^2$ | H | $OCH_3$ | $OCH_3$ | $OCHF_2$ |
| $V^3$ | H | $OCH_2CF_3$ | $CH_3$ | H |
| $V^4$ | H | $O(CH_2)_3OCH_3$ | $CH_3$ | H |
| $V^5$ | H | $OCH_2CH(CH_2)_2$ | H | F |

Contrary to all of the current PPI formulations where the acid labile PPI is protected from exposure to acidic conditions usually by an enteric or oil coating, as disclosed herein the present invention allows the stabilisation of the PPI by conversion to a disulfide complex either in vitro or in vivo.

The present invention also provides stable, ready-to-use oral or injectable administrable acid stable PPI compositions in solid or liquid form suitable for direct administration as liquid, gels, pastes, powders, tablets or for filling into capsules for human or animal use. The compositions can optionally also comprise one or more auxiliaries or excipients.

The present invention also provides compositions comprising one or more compounds of the formula I as defined above. For example the invention provides dry powder or tablet formulations for the in vivo production of compounds of formula I as defined above that have one or more proton pump inhibitors as described above and one or more sulfhydryl compounds as described above.

The PPIs used in accordance with the invention have increased protection from acid inactivation in the stomach and are efficiently absorbed directly into the stomach region. Compositions of the invention are of high potency and bioavailability.

PPIs contemplated herein for use in accordance with the present invention include Omeprazole, Omeprazole isomers such as S-Omeprazole, Esomeprazole (Nexium®), R-Omeprazole, Lansoprazole, Pantoprazole, Rabeprazole, Pariprazole, Tantoprazole, Leminoprazole, together with their isomers, pharmaceutically acceptable salts thereof as well as their metabolic prodrug forms. However, those skilled in the art will appreciate that the invention is not so limited, but that any pharmaceutically acceptable PPI may be employed. The disulfide compound that results from the reaction of the PPI and the sulfhydryl compound is stable under stomach acidic conditions and when formulated into a solid dosage form, the formulation does not need to be enterically coated.

U.S. Pat. No. 6,093,743 refers to creation of a "prodrug of proton pump inhibitors" by producing a hydrolysable sulfinyl or arylsulfonyl group attached to the benzimidazole nitrogen or includes a group that forms a Mannich base with the benzimidazole nitrogen. Applicant believes such a compound remains unstable to acid conditions.

PPIs are also themselves classed as pro-drugs which after administration are altered to a tetracycline sulfenamide with a terminal thiol group, which is the active form of the drug binding to the cysteine residue(s) in the H+/K+ ATPase gastric proton pump in the secretory membrane of the parietal cell to form covalent disulfide bonds that inhibit the activity of the pump.

This binding process was originally thought to be irreversible but is now known to be reversed by glutathione and other endogenous reducing agents in parietal cells. This invention utilizes the ability of PPIs to reversibly bind with these types of reducing agents which has led to the development of stabilising proton pump inhibitors with increased bioavailability.

The present invention is applicable to any pharmaceutically acceptable compound (PAC) which contains a sulfhydryl, sulfinyl, sulfonyl or sulfonamide group which forms a covalent bond with the sulfhydral group of a pharmacologically acceptable thiol compound. The resulting compounds or complexes are stable in the acid conditions of the stomach, and on tissue absorption undergo disulfide interchange with relevant enzymes or proteins in the body.

To describe the transport mechanisms of PACs as di-sulfides which can rapidly exchange with other biological sulfhydryl and di-sulfide groups in the body, the present inventor has coined the term "Zipper Effect". While not wishing to be bound to any one theory, the inventor believes that this mechanism also temporarily opens up pathways by dynamic reversible disengagement of protein disulfide bonds. This Zipper Effect results in improved chemical transport and increased micro circulation or diffusion particularly of beneficial bio-chemicals. Other simple sulfur compounds such as N-acetyl-cysteine also typically disrupt protein disulfide bonds and is used as a mucolytic to thin out mucous fluid. Another example is the role of the simple plasma sulfur compounds glutathione and glutathione disulfide which are in a state of dynamic equilibria acting as a plasma reduction-oxidation buffer system.

The compounds of the present invention allow for optimization of suitable PAC/disulfide compound pairing. The dynamic REDOX reversible nature of a disulfide bond formation and the Zipper Effect mentioned above is believed to significantly facilitate bioavailability. The PAC and sulfhydryl content of compounds of the present invention provides improved therapeutic benefit as a consequence of reversible disulfide bond formation.

As disclosed herein the compounds of the present invention can be formed either in vitro as part of the formulation or in vivo by incorporating the unreacted PAC and thiol compound in the formulation.

Typically under aqueous conditions, a PAC as herein before described can react with a thiol compound as hereinbefore described, at a molar ratio between 1:2 to 1:10, optionally at a temperature between 5 to 40° C. The resulting compounds may be water soluble.

The di-sulfide compounds of the present invention or the PAC and thiol compound can be incorporated into typical pharmaceutical compositions such as liquids, emulsions, suppositories, solutions, plasters (for example TTS), gels, pastes, powders, tablets, granules, pellets, capsules, injectable, as well as confectionary and foodstuffs. The compounds and compositions according to the invention can be administered by any suitable route, such as orally, parenterally, intraveneously or percutaneously. The suitable route for administration will vary from case to case as will be appreciated by those skilled in the art.

Compositions of the invention may include additional ingredients commonly used in the formulation of human and veterinary medicines with the exception of substances which cause or contribute to catalytic oxidation reactions in the preparations such as metal based pigments or dyestuffs. For example, fragrances and flavouring agents such as caramel, carrot, apple, cinnamon, vanilla and the like; colouring agents such as approved F&C dyestuffs, natural colouring such as beta carotene and natural vegetable oil colouring components. (It should be noted that no metal based pigments or dyestuffs should be used which might contribute to catalytic oxidation reactions in the preparations). Natural sweeteners such as sugar, molasses solids, artificial sweeteners such as saccharins, cyclamates; REDOX buffers such as ascorbates, pH buffers, preservatives such as parabens; antioxidants such as BHT, BHA; viscosity and rheology agents such as natural or synthetic waxes and pharmaceutically acceptable diluents can be added.

Examples of pharmaceutically acceptable diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 1% to 99.9% by weight of the compositions.

Formulations suitable for oral administration may be presented in discrete units, such as capsules, sachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture such as to form a unit dosage. For example, a tablet may be prepared by compressing or moulding a powder or granules containing the active compound, optionally with one or more accessory ingredients. Compressed tablets may be prepared by compressing, in a suitable machine, the compound of the free-flowing, such as a powder or granules optionally mixed with a binder, lubricant, inert diluent, and/or surface active/dispersing agent(s). Moulded tablets may be made by moulding, in a suitable machine, the powdered compound moistened with an inert liquid binder.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Formulations suitable for buccal (sublingual) administration include lozenges comprising the active compound in a flavoured base, usually sucrose and acacia or tragacanth; and pastilles comprising the compound in an inert base such as gelatin and glycerin or sucrose and acacia.

Compositions of the present invention suitable for parenteral administration typically conveniently comprise sterile aqueous preparations of the active compounds, which preparations may be isotonic with the blood of the intended recipient. These preparations are typically administered intravenously, although administration may also be effected by means of subcutaneous, intramuscular, or intradermal injection. Such preparations may conveniently be prepared by admixing the compound with water or a glycine buffer and rendering the resulting solution sterile and isotonic with the blood. Injectable formulations according to the invention generally contain from 0.1% to 60% w/v of active compound(s) and are administered at a rate of 0.1 ml/minute/kg or as appropriate. Parenteral administration is a preferred route of administration for the compounds of the present invention.

Formulations suitable for rectal administration are typically presented as unit dose suppositories. These may be prepared by admixing the active compound with one or more conventional solid carriers, for example, cocoa butter, and then shaping the resulting mixture.

Compositions of the invention may also comprise one or more additional pharmacologically active ingredients. Examples include: tranquilizers (for example from the group of the benzodiazepines, e.g. diazepam), spasmolytic drugs (e.g. bletamiverine or camylofine), anticholinergic drugs (e.g. oxyphencyclimine or phencarbamide), local anesthetics (e.g. tetracaine or procaine), optionally also enzymes, vitamins or amino acids. For example, the compounds of formula I can be used in combination with other pharmaceutical compounds which buffer or neutralize gastric acid or which inhibit the secretion of acid, such as, for example, antacids (such as, magaldrate), $H_2$-receptor blockers (for example cimetidine, ranitidine), P-CAB inhibitors or gastrin antagonists. Such additional compounds may enhance the main action of the compound of formula I in an additive or superadditive sense, eliminate or reduce side-effects, and/or obtain a more rapid onset of action. Combination with NSAIDs (such as, for example, aspirin, etofenamate, diclofenac, indomethacin, ibuprofen or piroxicam) for preventing the gastrointestinal damage caused by the NSAIDs, or with antibacterial substances (such as, for example, cephalosporins, tetracyclins, penicillins, macrolides, nitroimidazoles or else bismuth salt) for controlling *Helicobacter pylori* is also possible. Antibacterial combination partners for compounds of the invention include, for example, meziocillin, ampicillin, amoxicillin, cefalothin, cefoxitin, cefotaxim, imipenem, gentamycin, amicacin, erythromycin, ciprofloxacin, metronidazole, clarithromycin, azithromycin and combinations thereof (e.g. clarithromycin+metronidazole and amoxicillin+clarithromycin).

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification individually or collectively, and any and all combinations of any two or more of said steps or features.

The present invention will now be described with reference to the following non-limiting examples.

Example 1

Proton pump inhibitor with a —S═O sulfinyl (oxidising) group can react with the sulfhydryl (reducing) group of, for example, N-acetyl cysteine according to the following chemical equation:

PAC-S═O+SH—C⇌PAC-S—S—C where PAC-S═O is a PPI and SH—C is a N-acetyl cysteine molecule or a cysteine residue group on an amino acid, peptide or protein. The PAC-S—S—C disulfide covalent bonded product is more stable than the original PPI in the presence of acids. PPIs are normally acid labile resulting in PPI metabolites which are either less active or inactive.

These compounds are in a state of dynamic equilibria with formation and disengagement of disulfide covalent bonds.

The covalent bonded PPI is capable of transferring from one coordination site to another. Thus a proportion of the bound PPI in the complex will be transferred to other cellular sites, plasma etc with a proportion reaching the parietal cell membrane where it binds to the cell proton pump cysteine residues forming a disulfide bond.

Example 2

Disulfide interchange can be illustrated by the following chemical equation:

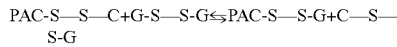

PAC-S—S—C+G-S—S-G⇌PAC-S—S-G+C—S—S-G where G-S—S-G is a typical glutathione di-sulfide product which can under go dynamic interchange with the PAC-S—S—C disulfide covalent bonded product.

The PAC may be derived from any compound with a residual sulfinyl group such as a PPI.

Example 3

Preparation of Omeprazole-N-Acetyl Cysteine Disulfide Complex In Vitro

The mole ratio of Omeprazole to N-Acetyl Cysteine should typically be a minimum 1:2 but more typically 1:2.5 or higher.

140 g of N-acetyl cysteine and 100 g of Omeprazole was added to 260 g of water at 20° C. and stirred over one hour until a clear solution was obtained. The reaction was slightly exothermic. Such reactions can typically rise in temperature to about 40° C. Larger batch sizes may require cooling to maintain the batch temperature below 40° C. The Omeprazole-N-acetyl cysteine disulfide solution was stored below 10° C.

Samples of the disulfide solution of Example 3 when analysed by HPLC showed the disulfide compound as an earlier peak with a shorter retention time than Omeprazole. The parameters used in the HPLC analysis were as follows:
Instrumental Parameters:
Instrument: Waters HPLC
Column: Zorbax Eclipse C18, 4.6×150 mm
Guard Column: C18
UV Detector Wave Length: 300 nm
Mobile Phase Composition: 30 Parts Acetonitrile to 70 Parts Phosphate Buffer pH 7.5
Flow Rate: 1 ml per minute
Run Time: 20 minutes
Injection Volume: 10 microliters The HPLC data appears in FIG. 1 and the relevant retention time data is shown below in Table 2:

Other proton pump inhibitors or PACs referred to herein can be made in a similar fashion.

The disulfide compounds in these examples may be recrystallised, or recovered by HPLC, or other established techniques, and then formulated into tablets, powders, pastes, capsules, injectable or other dosage forms.

Example 4

Human or Veterinary Powder Formulation for in vivo Formation of Omeprazole-N-Acetyl Cysteine Disulfide Complex The mole ratio of Omeprazole or Omeprazole salts to N-acetyl cysteine should typically be a minimum 1:2 but more typically 1:2.5 or higher.

The following powdered ingredients were mixed together in the proportions shown:

| All ingredients were preferably minus 100 mesh (particle size) | |
|---|---|
| Omeprazole (or its pharmaceutically acceptable salts) | 30 g |
| N-Acetyl Cysteine | 30 g |
| Light Magnesium Oxide | 40 g |
| TOTAL | 100 g |

The dry powder blend can be stored in sealed containers at 5 to 15 degrees Celsius until required.

Figure 2:
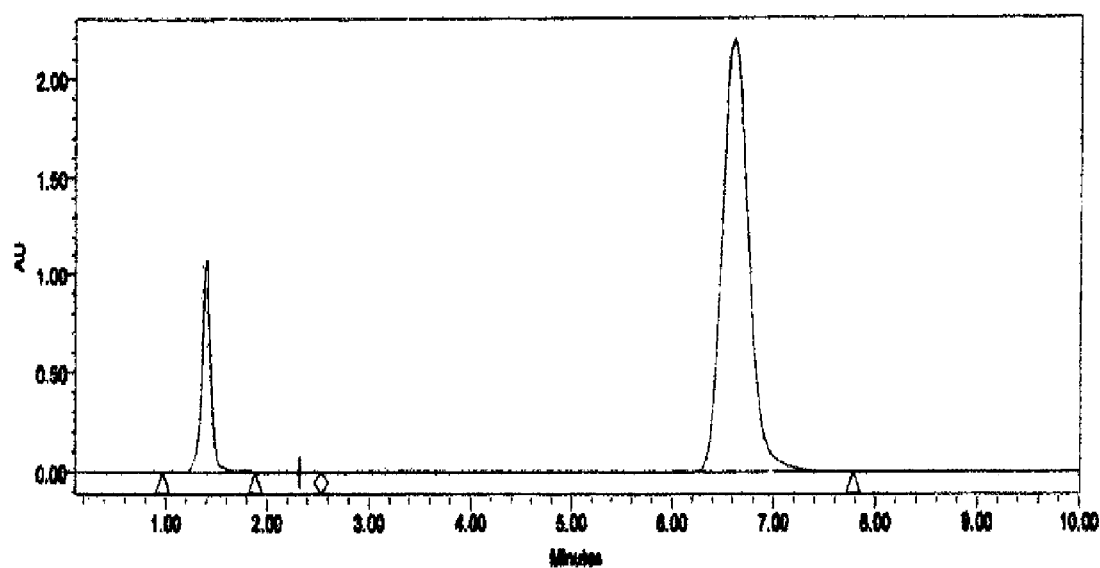
FIG. 2 shows the high performance liquid chromatograph for a sample of a dry powder blend of Omeprazole, N-acetyl cysteine disulfide and light magnesium oxide that was prepared in accordance with Example 4 and stored for 12 months before high performance liquid chromatograph (HPLC) analysis.

Stored samples of the dry powder blend of Example 4 when analysed by HPLC after 12 months showed an unreacted Omeprazole peak and an unreacted N-acetyl cysteine peak indicating that the Omeprazole had not reacted with the N-acetyl cysteine. The parameters used in the HPLC analysis were as follows:
Instrumental Parameters:
Instrument: Waters HPLC
Column: Zorbax Eclipse C18, 4.6×150 mm
Guard Column: C18
UV Detector Wave Length: 300 nm
Mobile Phase Composition: 30 Parts Acetonitrile to 70 Parts Phosphate Buffer pH 7.5
Flow Rate: 1 ml per minute
Run Time: 20 minutes
Injection Volume: 10 microliters The HPLC data appears in FIG. 2 and the relevant retention time data is shown below in Table 3:

TABLE 2

HPLC Data for Omeprazole-N-acetyl cysteine disulfide solution prepared in accordance with Example 3

| | Name | RT | Response | Area | Height | Amount | Units |
|---|---|---|---|---|---|---|---|
| 1 | Omep/Acetyl Cysteine complex | 1.5530 | 1.638e+007 | 16384742.4788 | 2254488.0040 | | |
| 2 | Omep/Acetyl Cysteine complex | 1.5534 | 1.639e+007 | 16386541.8949 | 2255204.7074 | | |
| Mean | | 1.6 | | 16385642.2 | 2254846.4 | | |

TABLE 3

HPLC Data for Dry Powder Blend of Omeprazole, N-acetyl cysteine and light Magnesium Oxide prepared in accordance with Example 4

|   | Name | T | Response | Area | Height | Amount | Units |
|---|------|---|----------|------|--------|--------|-------|
| 1 | N-Acetyl Cysteine | 1.4018 | 6.251e+006 | 6250647.0001 | 990517.4728 | | |
| 2 | Omeprazole | 6.5976 | 4.008e+007 | 40077098.8191 | 2190088.4535 | | |
| Mean | | 4.0 | | 23163872.9 | 1590303.0 | | |

As can be seen from Table 3, the typical retention time for N-acetyl cysteine is approximately 1.40 minutes. The typical retention time for Omeprazole is approximately 6.59 minutes. The typical retention time for the Omeprazole-N-acetyl cysteine disulfide is approximately 1.56 minutes as can be seen in Table 2 of Example 3.

The dry powder blend can be added directly to food or just prior to use can be mixed with water to make a stable suspension for oral or nasal tube administration to humans or animals.

Example 5

Preparation of Omeprazole Plus N-Acetyl Cysteine Human Application Tablets for In Vivo Formation of Disulfide Complex The following ingredients were mixed together in the proportions shown:

| All ingredients were preferably minus 200 mesh (particle size) | |
|---|---|
| Omeprazole | 20 mg |
| N-Acetyl Cysteine | 40 mg |
| Light Magnesium Oxide | 100 mg |
| Croscarmellose sodium | 7.0 mg |
| Magnesium stearate | 3.0 mg |
| and auxiliaries/excipients up to | 350 mg. |

The mixture was compressed into tablets having a weight of 350 mg per tablet, so that each tablet contained 20 mg of Omeprazole which was the label claim. The tablet required no enteric coating.

The conversion of the Omeprazole to the acid stable Omeprazole-N-Acetyl Cysteine disulfide compound took place in vivo and the formulations required no enteric coating.

Other proton pump inhibitors or PACs referred to herein can be formulated in a similar fashion and then formulated into powders, tablets, capsules, pastes, pellets, granule, injectable or other dosage forms.

Example 6

Preparation of Omeprazole Plus N-Acetyl Cysteine Human Injectable

The following ingredients were mixed together in the proportions to give a clear solution.

| Omeprazole | 20 mg |
|---|---|
| N-Acetyl Cysteine | 70 mg |
| Water for Injection | 5 ml |

Stored at 0-5 degrees Celsius in amber vials.

Example 7

Preparation of Omeprazole-N-Acetyl Cysteine Horse Paste

Mixed 100 grams of Omeprazole-N Acetyl Cysteine disulfide solution as prepared in Example 3 with 2 grams of xanthan gum to make a paste.

Biological Examples

Samples prepared in Examples 4, 6 and 7 were tested on horses.

The protocol adopted was to administer the samples to the horses with their evening food then withdraw access to water for the following 20 hours. During the 15 to 19 hour period small samples of stomach fluid were withdrawn for pH measurement.

Control samples were run based on a commercial Omeprazole oil based product and an enteric coated product. All were dosed at the equivalent of 4 mg of Omeprazole per kg of horse body weight.

| Omeprazole Based Products | Stomach Fluid pH after 15 Hours | Stomach Fluid pH after 19 Hours |
|---|---|---|
| Nil Product Control | 5.2 | 2.8 |
| Commercial Oil based Paste | 5.1 | 4.9 |
| Commercial Enteric Coated paste | 4.8 | 4.7 |
| Example 4 Powder | 5.0 | 4.9 |
| Example 6 Injectable | 5.1 | 4.9 |
| Example 7 Paste | 5.0 | 4.8 |

As the tests on the above samples show, the acid suppression activity of the Omeprazole-N-Acetyl Cysteine disulfide either as the in vivo type powder formulation of Example 4, the in vitro injectable of Example 6 or the in vitro formulation of Example 7 compared well with the commercially available oil and enteric coated type products.

What is claimed is:

1. A compound having the structure (A):

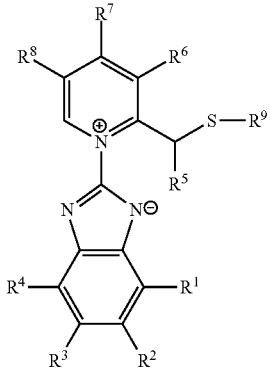

(A)

wherein $R^1$, $R^2$, $R^3$ and $R^4$ are the same or different and are hydrogen, an alkyl, cycloalkyl, alkoxy, alkoxyalkyl, alkoxyalkoxy, halogen, —CN, —CF$_3$, —NO$_2$, —COR$^{10}$, alkylthio, alkylsulfinyl, aryl, arylalkyl, aryloxy or arylalkoxy group, or wherein $R^1$ and $R^2$, $R^2$ and $R^3$, or $R^3$ and $R^4$ together with the adjacent carbon atoms in the benzimidazole ring form one or more 5-, 6- or 7-membered rings, which each may be saturated or unsaturated and may contain 0-3 hetero atoms selected from N, S and O, and each ring may be optionally substituted with 1-4 substituents selected from alkyl groups with 1-3 carbon atoms, or two or four of the mentioned substituents together form one or two oxo groups

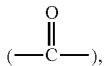, or $R^1$ and $R^2$, $R^2$ and $R^3$ or $R^3$ and $R^4$ together with the adjacent carbon atoms in the benzimidazole ring form two rings condensed with each other;

$R^5$, $R^6$ and $R^8$ are the same or different and are selected from hydrogen and alkyl;

$R^7$ is hydrogen, an alkyl, alkoxy, aryl, arylalkyl, aryloxy, arylalkoxy, alkenyloxy or alkynyloxy group; or $R^6$ and $R^7$, or $R^7$ and $R^8$ together with the adjacent carbon atoms in the pyridine ring form a 5- or 6-membered, saturated or unsaturated ring, which may optionally contain an oxygen or an optionally alkylated nitrogen atom, $R^{10}$ represents alkyl, aryl, aryloxy and alkoxy, and $R^9$ is a radical of a pharmacologically acceptable sulfhydryl compound, wherein the sulfhydryl compound is selected from the group consisting of N-acetyl-cysteine, penicillamine, thioalkl(alkene)ols, thiosorbitol, thioglycerol, thioglucose, thioacetic acid, thiomalic acid, thiopolyoxyethanols, thiopolyalkoxyethanols, thiouracil, thioguanosine, thiolhistidine and thionalide, with the proviso that the compound having the structure (A) is other than

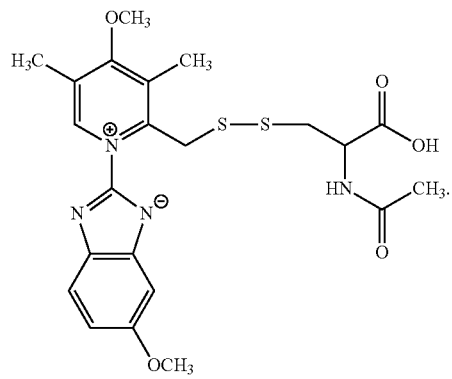 [SMILES: COc1ccc2nc(-[n+]3cc(C)c(OC)c(C)c3CSSCC(NC(C)=O)C(=O)O)[n-]c2c1]

2. A compound according to claim 1 wherein $R^9$ is N-acetyl cysteine.

3. A compound having the structure (V):

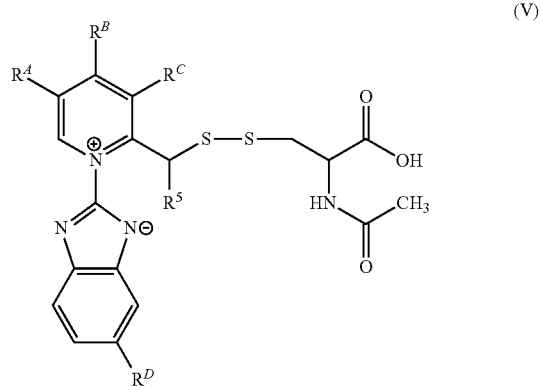

(V)

wherein:

$R^A$, $R^B$ and $R^C$ independently represent hydrogen, C$_{1-6}$ alkyl, C$_{1-6}$ alkoxy, C$_{3-6}$ cycloalkyl, C$_{3-6}$ cycloalkoxy, C$_{1-6}$ fluoroalkyl or C$_{1-6}$ fluoroalkoxy; $R^5$ is hydrogen or alkyl and $R^D$ represents hydrogen, C$_{1-6}$ alkyl, C$_{1-6}$ alkoxy, C$_{1-6}$ fluoroalkyl or C$_{1-6}$ fluoroalkoxy or halogen, with the proviso that the compound having the structure (V) is other than

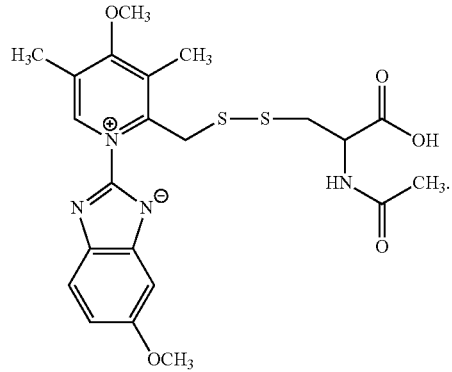 [SMILES: COc1ccc2nc(-[n+]3cc(C)c(OC)c(C)c3CSSCC(NC(C)=O)C(=O)O)[n-]c2c1]

* * * * *